(12) United States Patent
Kamarajugadda et al.

(10) Patent No.: US 10,384,050 B2
(45) Date of Patent: Aug. 20, 2019

(54) IMPLANTABLE MEDICAL LEAD CONDUCTOR HAVING CARBON NANOTUBE WIRE

(71) Applicants: Mallika Kamarajugadda, Eden Prairie, MN (US); Mark Breyen, Champlin, MN (US); Suping Lyu, Maple Grove, MN (US); Bernard Q. Li, Plymouth, MN (US); Qin Zhang, Shoreview, MN (US); Jacob Popp, Maplewood, MN (US); Medtronic, Inc., Minneapolis, MN (US)

(72) Inventors: Mallika Kamarajugadda, Eden Prairie, MN (US); Mark Breyen, Champlin, MN (US); Suping Lyu, Maple Grove, MN (US); Bernard Q. Li, Plymouth, MN (US); Qin Zhang, Shoreview, MN (US); Jacob Popp, Maplewood, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

(21) Appl. No.: 15/316,482

(22) PCT Filed: Jun. 24, 2015

(86) PCT No.: PCT/US2015/037379
§ 371 (c)(1),
(2) Date: Dec. 5, 2016

(87) PCT Pub. No.: WO2015/200459
PCT Pub. Date: Dec. 30, 2015

(65) Prior Publication Data
US 2017/0189669 A1    Jul. 6, 2017

Related U.S. Application Data (60) Provisional application No. 62/016,910, filed on Jun. 25, 2014.

(51) Int. Cl.
*A61N 1/00* (2006.01)
*G01R 33/28* (2006.01)
(Continued)

(52) U.S. Cl.
CPC .............. *A61N 1/00* (2013.01); *A61N 1/04* (2013.01); *A61N 1/05* (2013.01); *A61N 1/3718* (2013.01);
(Continued)

(58) Field of Classification Search
CPC .......... A61N 1/00; A61N 1/04; A61N 1/3718; A61N 1/05; A61N 1/086; G01R 33/288; G01R 33/285
See application file for complete search history.

(56) References Cited

U.S. PATENT DOCUMENTS

2008/0195186 A1    8/2008 Li et al.
2009/0196982 A1    8/2009 Jiang et al.
(Continued)

OTHER PUBLICATIONS

PCT/US2015/037379, International Search Report, dated Jan. 6, 2016.
(Continued)

*Primary Examiner* — Mark Bockelman (57) ABSTRACT

An implantable medical leads has a conductor that includes one or more metal wires and one or more carbon nanotube wires extending in substantially the same direction as the one or more metal wires. Such conductors may result in less MRI-induced heating at electrodes of leads than conductors that do not contain carbon nanotubes.

10 Claims, 6 Drawing Sheets

(51) Int. Cl.
*A61N 1/37* (2006.01)
*A61N 1/05* (2006.01)
*A61N 1/04* (2006.01)
*A61N 1/08* (2006.01)

(52) U.S. Cl.
CPC ......... *G01R 33/285* (2013.01); *G01R 33/288* (2013.01); *A61N 1/086* (2017.08)

(56) References Cited

U.S. PATENT DOCUMENTS

| | | |
|---|---|---|
| 2010/0217262 A1 | 8/2010 | Stevenson et al. |
| 2013/0109905 A1 | 5/2013 | Qian et al. |
| 2013/0110212 A1 | 5/2013 | Feng et al. |
| 2013/0110213 A1 | 5/2013 | Feng et al. |
| 2013/0158643 A1 | 6/2013 | Wang et al. |
| 2014/0068935 A1 | 3/2014 | Li et al. |

OTHER PUBLICATIONS

European Office Action for Patent Application No. EP 15734002.7, dated Mar. 29, 2018; 4 pages.

IMPLANTABLE MEDICAL LEAD CONDUCTOR HAVING CARBON NANOTUBE WIRE

RELATED APPLICATION

This application claims the benefit of U.S. Provisional Patent Application No. 62/016,910, filed on Jun. 25, 2014.

FIELD

This disclosure generally relates to, among other things, implantable medical leads; and more particularly to electrical conductors that result in low levels of heating at an electrode when the leads are subjected to magnetic resonance imaging.

BACKGROUND

Implantable medical leads typically have a contact for electrical connection to an active implantable medical device and an electrode coupled to the contact via a conductor. The conductor carries electrical signals from the device to the electrode or from the electrode to the device. Leads and conductors are typically insulated such that only the electrodes are in electrical contact with a patient's body when implanted.

Patients in which medical leads are implanted may, on occasion, undergo magnetic resonance imaging (MRI) procedures to diagnose a condition, which may or may not be related to a condition for which the implanted lead is intended to treat or monitor. Regardless of the reason for the MRI procedure, MRI can result in heating of the conductor induced by the radio frequency (RF) field in MRI. Because the conductor and lead body is typically insulated, the heat tends to concentrate at the exposed electrode. Such heating of the electrode can be undesirable if the temperature rise is large or sustained.

A number of solutions have been developed to produce MRI-safe leads. However, additional developments in the production of MRI-safe leads would be desirable.

SUMMARY

This disclosure describes, among other things, implantable medical leads having a conductor that includes one or more metal wires and one or more carbon nanotube wires extending in substantially the same direction as the one or more metal wires. Such conductors may result in less MRI-induced heating at electrodes of leads than conductors that do not contain carbon nanotubes.

In some embodiments, a conductor includes at least one metal wire in contact in contact with at least one carbon nanotube wire. In some embodiments, one or more metal wires and one or more carbon nanotube wires are twisted or braided to form the conductor. In some embodiments, one or more metal wires and one or more carbon nanotube wires together form strands that are then braided to form the conductor. In some embodiments, the one or more metal wires occupy 5% or more of the cross sectional area of the conductor. In some embodiments, the one or metal wires occupy 50% or less of the cross sectional area of the conductor.

One or more embodiments of the systems, leads, conductors, strands, wires or methods described herein provide one or more advantages over prior systems, leads, conductors, strands, wires or methods. Such advantages will be readily understood from the following detailed description.

The schematic drawings in are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

This disclosure describes, among other things, implantable medical leads having a conductor that includes one or more metal wires and carbon nanotubes. In some embodiments, conductor includes one or more metal wires and one or more carbon nanotube wires extending in substantially the same direction as the one or more metal wires. Such conductors may result in less MRI-induced heating at electrodes of leads than conductors that do not contain carbon nanotubes.

In some embodiments, an implantable medical lead as described herein has an electrode that heats by less than about 5° C. when the lead is subjected to MRI. For purposes of the present disclosure, subjecting a lead to MRI means subjecting the lead to MRI parameters that a patient would typically experience during an MRI procedure. For example, the lead may be subjected to 1.5 T MRI scan at normal operating mode or an equivalent thereof. Preferably, the electrode heats by about 5° C. or less, less than about 4° C., less than about 3° C., or less than about 2° C. when subjected to MRI.

Heating of an electrode may be tested in any suitable manner. In some embodiments, heating of an electrode is evaluated by an in-vitro measurement that is able to predict in-vivo lead electrode heating. In some embodiments, heating of an electrode of a lead subjected to MRI can be tested by employing a method that characterizes the electrical property of the lead under corresponding MRI frequencies. In some embodiments, the lead is evaluated in tissue. In some embodiments, the lead is evaluated using modeling. In some embodiments, the lead is evaluated using a combination of one or more of the above methods.

In some embodiments, an electrode of an implantable medical lead heats by less than about 5° C. (e.g., less than about 4° C., less than about 3° C., or less than about 2° C.) when the lead is subjected to MRI under the following conditions: 1.5 T MRI scan at normal operating mode, and where heating at the electrode is tested by an in-vitro measure that is predictive of in-vivo electrode heating.

Examples of predictive modelling that may be used or modified are disclosed in Wilkoff et al., Safe magnetic resonance imaging scanning of patients with cardiac rhythm devices: A role for computer modeling, Heart Rhythm 10(12), December 2013, pp. 1815-1821. Such predictive models may include RF coil models, human body models, lead models, lead routing models and model validation (e.g., similar to that described in Wilkoff et al.).

Of course, not all embodiments of leads described herein, relative to leads having conductors without carbon nanotube wires, will result in less heating at an electrode when the lead is subjected to MRI. However, in preferred embodiments, less MRI-induced heating results.

In some embodiments, an electrode of a lead having a conductor as described herein results in decreased heating relative to an electrode of a substantially similar lead having a conductor formed from a single copper wire with a diameter of about 30 microns coated with an insulator to have a total diameter of about 0.1 mm. The substantially similar lead may be the same lead with the carbon nanotube/metal conductor removed and the insulated copper conductor inserted and operably coupled in place of the removed carbon nanotube/metal conductor. Alternatively, the substantially similar lead may be a lead manufactured or assembled in a manner that is the same as the lead having the conductor as described herein except that the conductor is replaced with the insulated copper wire conductor. In some embodiments, the heating at the electrode of the lead having a carbon nanotube/metal conductor operably coupled to the electrode is reduced by 50% or more relative to the electrode of the substantially similar lead having the insulated copper conductor. In some embodiments, heating is reduced by 60% or more, by 70% or more, or by 80% or more. Reduced relative heating may be determined by comparing heating of the lead in ex-vivo in a laboratory setting or by predictive modeling as described above.

In some embodiments, a lead includes one or more metal wires and one or more carbon nanotube wires extending in substantially the same direction as the one or more metal wires. For purposes of the present disclosure a carbon nanotube wire extending in substantially the same direction as a metal wire is a carbon nanotube wire that is parallel to the metal wire, that is twisted together with the metal wire, that is braided together with the metal wire, or the like. A carbon nanotube wire that is spirally wound around a metal wire would not be considered to be extending in substantially same direction as the metal wire for purposes of the present disclosure.

Figure 1:
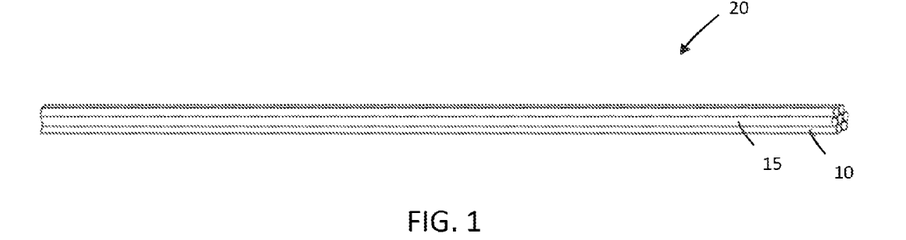
FIG. 1 is a schematic perspective view of an embodiment of a parallel strand including at least one metal wire and at least one carbon nanotube wire.

Referring now to FIG. 1, a strand 20 of wires that includes at least one carbon nanotube wire 10 and at least one metal wire 15 is shown. A strand 20 may include any number of metal wires and carbon nanotube wires. In some embodiments, a strand 20 consists of one metal wire and a plurality of carbon nanotube wires. In some embodiments, a strand 20 includes a core of more than one metal wire surrounded by a plurality of carbon nanotube wires (such as carbon nanotube yarns) surrounding the core. The use of multiple metal wires allows of an increase in area of the metal core, which should improve conductivity, while also improving fatigue performance relative to using one large diameter metal wire. In some embodiments, a strand 20 includes at least one metal wire 15 in contact with at least one carbon nanotube wire 10.

Figure 2:
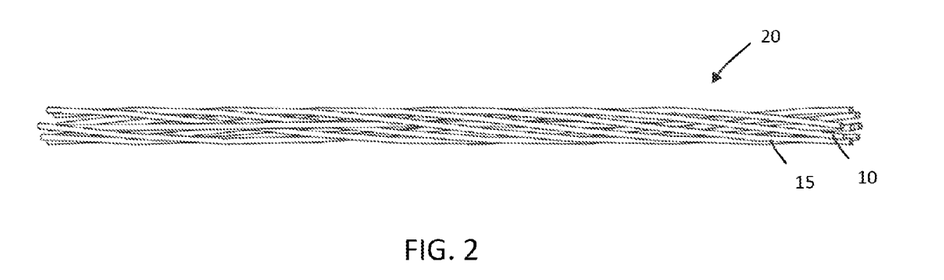
FIG. 2 is a schematic perspective view of an embodiment of a twisted strand including at least one metal wire and at least one carbon nanotube wire.

As shown in FIG. 2 a strand 20 of one or more metal wires 15 and one or more carbon nanotube wires 10 may be a twisted strand in which the wires are twisted relative to one another. The wires may also be braided to form a braided strand (not shown). A strand can contain any suitable numbers of wires. In some embodiments, a strand includes three, five, seven, or nineteen wires.

Figure 3A:
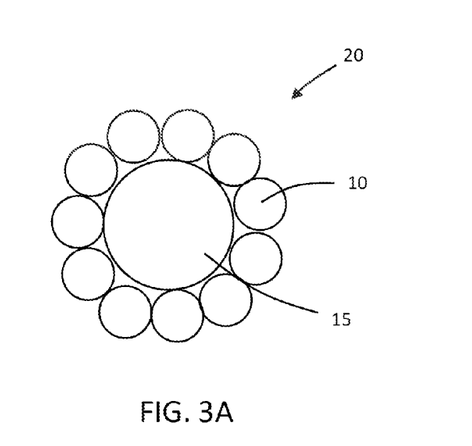
FIG. 3A is a schematic radial cross-sectional view of an embodiment of a strand including at least one metal wire and at least one carbon nanotube wire.

Regardless of whether the strands are parallel stands (see, e.g., FIG. 1), twisted stands (see, e.g., FIG. 2) or braided strands, a radial section of the strand have a similar appearance. By way of example, a radial cross section of a strand 20 having one metal wire 15 and a plurality of carbon nanotube wires 10 is shown in FIG. 3A. The metal wire 15 in the depicted section is in the middle of the strand 20 and the carbon nanotube wires 10 are disposed around the metal wire. It can be appreciated that the section shown in FIG. 3A could be a section at a particular location of a parallel strand, a twisted strand of a braided strand.

Figure 3B:
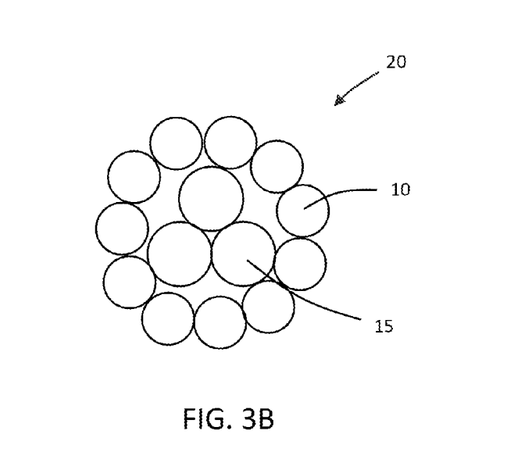
FIG. 3B is a schematic radial cross-sectional view of an embodiment of a strand including more than one metal wire and at least one carbon nanotube wire.

By way of another example, a radial cross section of a strand 20 having three metal wires 15 and a plurality of carbon nanotube wires 10 is shown in FIG. 3B. The metal wires 15 in the depicted section is in the middle of the strand 20 and the carbon nanotube wires 10 are disposed around the metal wires. As indicated above, the use of multiple metal wires allows of an increase in area of the metal core, which should improve conductivity, while also improving fatigue performance relative to using one large diameter metal wire.

Any suitable carbon nanotube wire may be used in a strand. In embodiments, the carbon nanotube wire consists of, or consists essentially of, carbon nanotubes. Carbon nanotubes wires may be carbon nanotube wires as described in, for example, U.S. Published Patent Application No. 2013/0110213, published on May 2, 2013, and entitled PACEMAKERS AND PACEMAKER LEADS. A carbon nanotube wire can be a non-twisted carbon nanotube wire or a twisted carbon nanotube wire.

A twisted carbon nanotube wire can include a plurality of carbon nanotubes oriented around an axis of the twisted carbon nanotube wire; e.g., like a helix. A twisted carbon nanotube wire can include a number of carbon nanotubes joined end to end by van der Waals attractive force. A twisted carbon nanotube wire can be formed by applying a mechanical force to turn two ends of a drawn carbon nanotube film in opposite directions. A carbon nanotube film may be a carbon nanotube film as described in, for example, U.S. Published Patent Application No. 2013/0110213.

A non-twisted carbon nanotube wire can include a plurality of carbon nanotubes oriented along a direction along the length of the wire. The carbon nanotubes can be parallel to the longitudinal axis of the wire. Non-twisted carbon nanotube wire can include a number of carbon nanotube segments joined end to end by van der Waals attractive force. A non-twisted carbon nanotube wire can be formed by treating a drawn carbon nanotube film (e.g., as described in U.S. Published Patent Application No. 2013/0110213) with an organic solvent. For example, a drawn carbon nanotube film can be treated by applying the organic solvent to the drawn carbon nanotube film to soak a surface of the carbon nanotube film. After being soaked by the organic solvent, the adjacent paralleled carbon nanotubes in the drawn carbon nanotube film tend to bundle together, thereby shrinking into a non-twisted carbon nanotube wire. Preferably, the organic solvent is volatile.

Carbon nanotubes in a carbon nanotube wire can be single-walled carbon nanotubes, double-walled carbon nanotubes, multi-walled carbon nanotubes, or combinations thereof. Diameters of carbon nanotubes are typically in the range from about 0.5 nanometers to about 50 nanometers. The carbon nanotubes in a carbon nanotube can have any height. In some embodiments, heights of carbon nanotubes in a carbon nanotube wire are from about 50 nanometers to about 5 millimeters, such as from about 100 microns to 900 microns.

A carbon nanotube wire, whether twisted, non-twisted or otherwise, may have any suitable diameter. In some embodiments, a carbon nanotube wire may have a diameter of from about 0.0001 inch to about 0.01 inch, such as from about 0.0002 inch to about 0.008 inch, or from about 0.0005 inch to about 0.005 inch. Preferably, the diameter of a carbon nanotube wire is about 0.02 inch or less. For purposes of the present disclosure, a carbon nanotube wire can be a bundle (e.g., parallel, twisted, braided, yarn, etc.) of more than one carbon nanotube wire.

Because of desirable mechanical properties of carbon nanotube wires, small diameter carbon nanotube wires can have suitable strengths. Accordingly, overall dimensions of conductors that include carbon nanotube wires and leads that include such conductors can be kept small if desired.

However, carbon nanotube wires tend to have substantially lower conductivity than metal counterparts. For example, some carbon nanotube wires can have a conductivity of about ten times less than a MP35N wire. Accordingly, the conductors described herein include a metal wire.

Any suitable metal wire may be used in a strand. Examples of metals that may be used to form a wire include copper, gold, silver, platinum, a nickel-cobalt-chromium-molybdenum alloy such as MP35N, tantalum, molybdenum, tungsten, platinum-iridium, palladium, cobalt-chromium, other metals or alloys, and the like, and combinations thereof. A metal wire may have any suitable thickness or diameter. Metal wires for use in leads typically have diameters from about 0.001 inch to about 0.01 inch. However, due to mechanical performance of carbon nanotubes in the strands, smaller diameter metal wires may be used. In some embodiments, a metal wire has a diameter of from about 0.0005 inch to about 0.005 inch.

Figure 4:
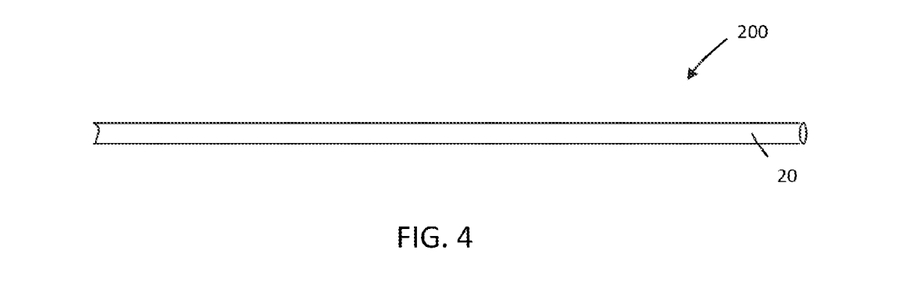
FIG. 4 is a schematic perspective view of an embodiment of a conductor, where the conductor is a strand.
Figure 5:
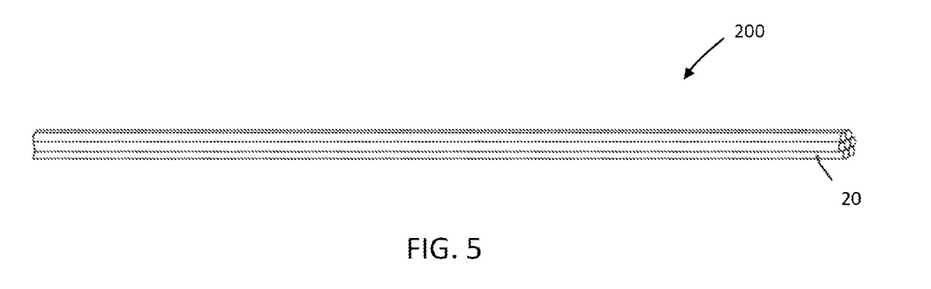
FIG. 5 is a schematic perspective view of an embodiment of a conductor having parallel strands.
Figure 6:
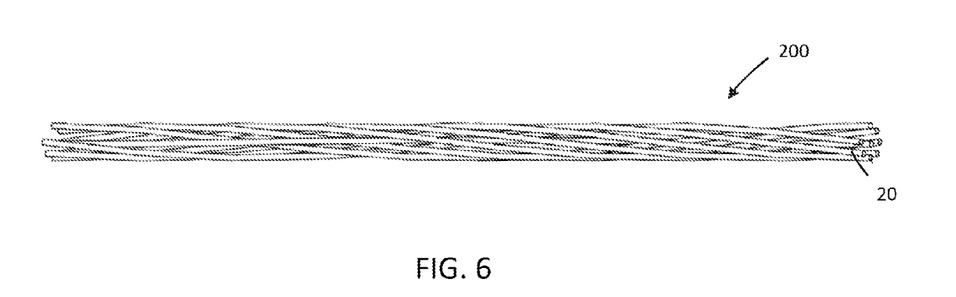
FIG. 6 is a schematic perspective view of an embodiment of a conductor having strands twisted around one another.

Referring now to FIG. 4, a strand 20 may form a conductor 200. Alternatively, a conductor 200 may comprise a plurality of strands 20 that may be parallel (e.g., FIG. 5), twisted around one another (e.g., FIG. 6), braided, or the like. A conductor 200 may contain any suitable number of strands 20. In some embodiments, a conductor includes one strand, three strands, seven strands, or nineteen strands.

In some embodiments, a conductor is oriented in a 1×7, 7×7, 1×19, or 1×3 configuration, where the first number indicates the number of wires in a strand and the second number indicates the number of strands in conductor. Of course, a conductor may have any other suitable configuration. For purposes of the present disclosure, where there is one wire in a strand (e.g., 1×7, 1×19, 1×3) the combination of wires can be considered the strand and the strand can thus be considered the conductor. For example, if a 1×7 configuration is employed, the conductor can be considered to be of a single strand having seven wires.

Regardless of the configuration of a conductor, a ratio of radial cross-sectional area of metal to carbon nanotube is preferably at least about 1:50 or at least about 1:20. Such a ratio should provide sufficient conductivity due to the metal to serve as a suitable conductor for a lead while taking advantage of the mechanical properties of carbon nanotube wires. In some embodiments, the ratio of radial cross-sectional area of metal to carbon nanotube is from about 1:20 to about 1:1, such as from about 1:10 to about 1:1 or about 1:5 to about 1:1.

Figure 7:
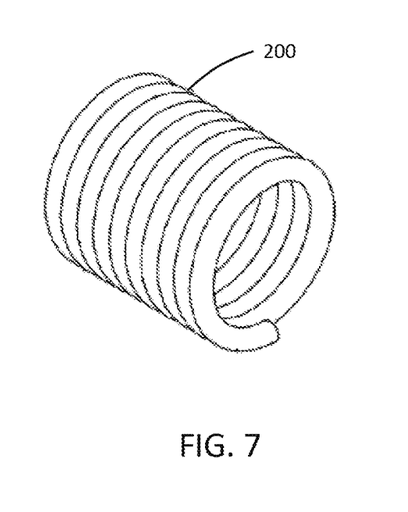
FIG. 7 is a schematic perspective view of a portion of an embodiment of a conductor.

Typically, a conductor in an implantable medical lead is coiled (see, e.g., conductor 200 in FIG. 7). The conductor 200 may be coiled prior to, or as a part of, assembling a lead.

Figure 8:
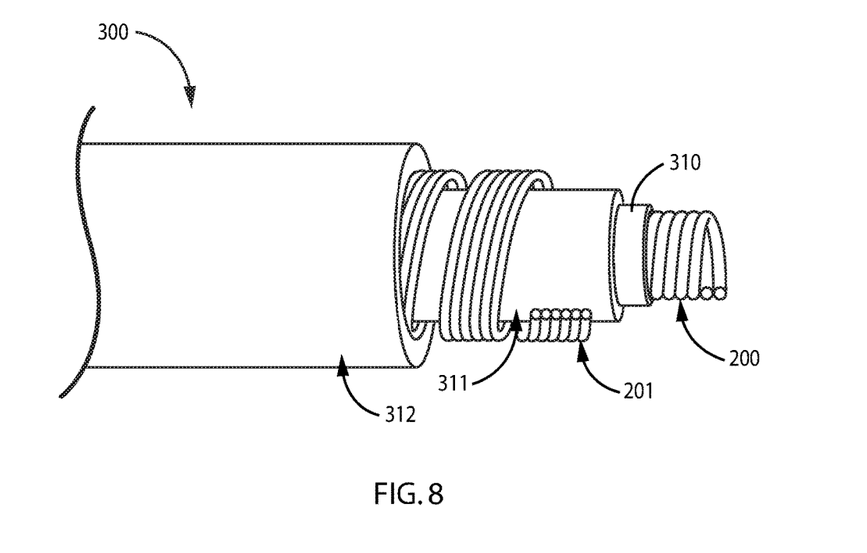
FIG. 8 is a schematic partial cut away perspective view of an embodiment of a lead.

Referring now to FIG. 8, a partial cut-away perspective view of an embodiment of a lead 300 is shown. The lead includes two coiled conductors 200, 201. A layer of insulating material 310 is disposed over conductor 200, while conductor 201 is spirally wound over insulating material 310. A layer of insulating material 312 is disposed over conductor 201 and serves as the outer layer of the lead 300. The lead depicted in FIG. 8 is shown for purposes of example.

It will be understood that a lead may have any suitable number of conductors and any suitable configuration. Insulating layers may be coated, or otherwise disposed, on an underlying layer or structure. Insulating layer is electrically insulating and is preferably biocompatible. Where a lead includes more than one insulating layer, it will be understood that the materials, thicknesses, etc. of the insulating layers may be the same or different. Examples of materials that are suitable for insulating layers of leads include silicon, polyurethane, polytetrafluoroethylene, poly(ethylene-co-tetrafluoroethylene), polyimide, copolymers of silicon and polyurethane, and the like. Insulating layers may have any suitable thickness. For example, insulating layers can have a thickness of from about 0.0001 inch to about 0.01 inch, such as from about 0.0003 inch to about 0.002 inch.

In some embodiments, a lead may include a shielding layer to prevent electromagnetic interference or the like. The shielding layer may be a conductive layer, such as metal layer or a carbon nanotube layer.

Any suitable implantable medical lead may include a conductor as described herein. For example, a lead may be a lead for providing therapy to a patient, a lead for monitoring a condition of a patient, or a lead for therapy and monitoring. Examples of such leads include leads for cardiac monitoring or therapy, brain and spinal cord monitoring or therapy, gastrointestinal monitoring or therapy, peripheral nerve monitoring or therapy, muscular monitoring or therapy, and the like. For example, a lead may be a pacemaker lead, a defibrillator lead, a cardiac resynchronization lead, a cardiac monitoring lead, a deep brain stimulation lead, a spinal cord stimulation lead, a peripheral nerve stimulation lead, or the like.

Such leads typically have a distal end portion having one or more electrodes for delivering therapy or monitoring a condition of a patient. The leads also have a proximal end portion having one or more electrical contacts configured to electrically couple with an active medical device, such as a signal generating device, a monitoring device, or the like. Examples of such active medical devices include a pacemaker, a defibrillator, a cardiac resynchronization device, a cardiac monitoring device, a deep brain stimulator, a spinal cord stimulator, a peripheral nerve stimulator, a gastro stimulator, and the like. The proximal contacts of the leads are electrically coupled to the electrodes via one or more conductors as described herein.

Figure 9:
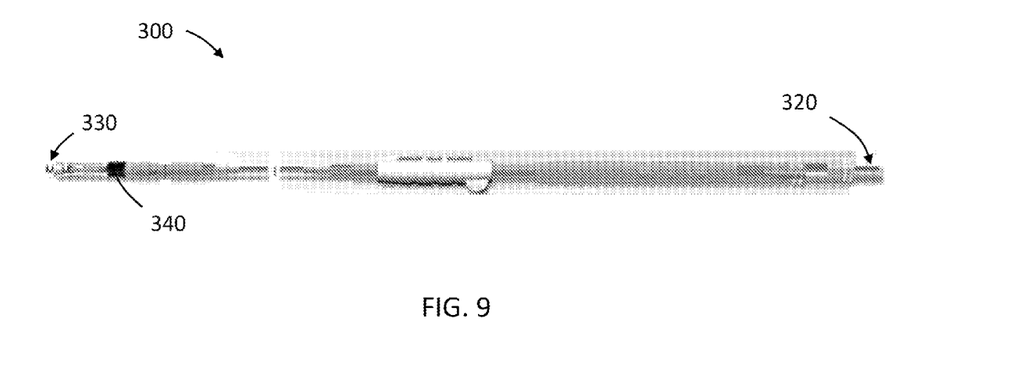
FIG. 9 is an image of a Medtronic, Inc. Model 5076 lead, which may be modified to include a conductor described herein.

For purposes of example, an image of a Medtronic, Inc. Model 5076 lead is depicted in FIG. 9. The lead 300 includes a connector pin 320 for electrically coupling the lead to an active medical device. The connector pin 320 includes two contacts. The lead 300 also includes two electrodes 330, 340 electrically coupled to the proximal contacts via conductors (not shown). Electrode 330 is a helical electrode that also serves as a fixation mechanism for anchoring the electrode in a patient's cardiac tissue. Electrode 340 in the 5076 lead is a ring electrode that may be used for monitoring or sensing. It will be understood that any lead having a contact, and electrode, and a conductor electrically coupling the contact to the electrode may be employed in accordance with the teachings presented herein and that the Medtronic, Inc. Model 5076 lead is presented merely for purposes of example.

Figure 10:
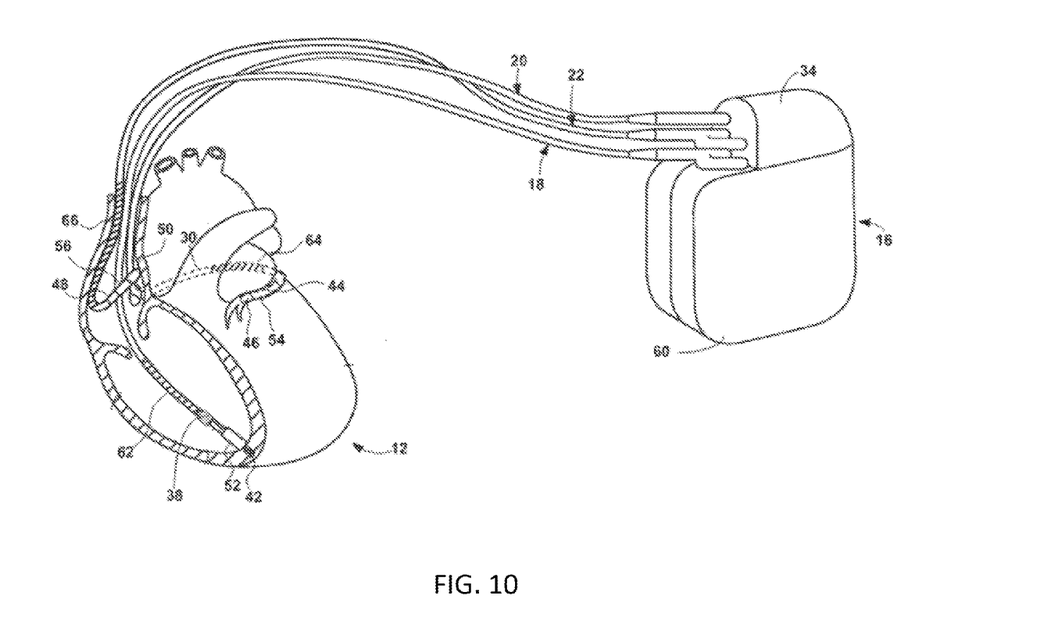
FIG. 10 is a conceptual view of an embodiment of an active medical device and embodiments of associated leads for monitoring or delivering therapy to a heart.

For purposes of further example, a conceptual schematic diagram of an embodiment of a system including an implantable active medical device, IMD, 16 and leads 18, 20, 22 is shown. Leads 18, 20, 22 may be electrically coupled to a stimulation generator, a sensing module, or other modules of IMD 16 via connector block 34. In some examples, proximal ends of leads 18, 20, 22 may include electrical contacts that electrically couple to respective electrical contacts within connector block 34. In addition, in some examples, leads 18, 20, 22 may be mechanically coupled to connector block 34 with the aid of set screws, connection pins or another suitable mechanical coupling mechanism.

Each of the leads 18, 20, 22 includes an elongated insulative lead body, which may carry a number of concentric coiled conductors separated from one another by tubular insulative sheaths. In the illustrated example, an optional pressure sensor 38, such as a capacitive or piezoelectric absolute pressure sensor, and bipolar electrodes 40 and 42 are located proximate to a distal end of lead 18. In addition, bipolar electrodes 44 and 46 are located proximate to a distal end of lead 20 and bipolar electrodes 48 and 50 are located proximate to a distal end of lead 22.

Electrodes 40, 44 and 48 may take the form of ring electrodes, and electrodes 42, 46 and 50 may take the form of extendable helix tip electrodes mounted retractably within insulative electrode heads 52, 54 and 56, respectively. It will be understood that any suitable electrode may be employed in accordance with the teachings presented herein and that the electrodes need not be limited to ring electrodes or helix tip electrodes. For example, electrodes may be small flat electrodes such as those used in paddle leads for spinal cord stimulation, electrodes that are electrodeposited on a substrate, or the like. Each of the electrodes 40, 42, 44, 46, 48 and 50 may be electrically coupled to a respective one of the coiled conductors within the lead body of its associated lead 18, 20, 22, and thereby coupled to respective ones of the electrical contacts on the proximal end of leads 18, 20 and 22.

Electrodes 40, 42, 44, 46, 48 and 50 may sense electrical signals attendant to the depolarization and repolarization of heart 12. The electrical signals are conducted to IMD 16 via the respective leads 18, 20, 22. IMD 16 may also deliver pacing pulses via electrodes 40, 42, 44, 46, 48 and 50 to cause depolarization of cardiac tissue of heart 12. In some examples, IMD 16 includes one or more housing electrodes which may be formed integrally with an outer surface of hermetically-sealed housing 60 of IMD 16 or otherwise coupled to housing 60. In some examples, housing electrode is defined by an uninsulated portion of an outward facing portion of housing 60 of IMD 16. Other division between insulated and uninsulated portions of housing 60 may be employed to define two or more housing electrodes. In some examples, housing electrode comprises substantially all of housing 60. Any of the electrodes 40, 42, 44, 46, 48 and 50 may be used for unipolar sensing or pacing in combination with housing electrode 58.

Leads 18, 20, 22 may also include elongated electrodes 62, 64, 66, respectively, which may take the form of a coil. IMD 16 may deliver defibrillation shocks to heart 12 via any combination of elongated electrodes 62, 64, 66, and housing electrode. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy, tantalum, tantalum alloys, MP35N, coated metals or other materials known to be usable in implantable defibrillation electrodes.

It will be understood that leads as described herein may be used with any suitable system, such as a deep brain stimulation system, a spinal cord stimulation system, a gastric stimulation system, a monitoring system, and the like, and that the cardiac stimulation and monitoring system presented in FIG. 10 is merely for purposes of example.

In some embodiments (not depicted), an implantable medical lead includes a proximal end portion having a contact, a distal end portion having an electrode, a conductor electrically coupling the electrode to the contact, and a carbon nanotube structure coupled to the electrode and the conductor, but not the contact. It is believed that the thermal conductive properties of the carbon nanotube structure may result in less heating at the electrode during MRI. In some embodiments, an electrode of such an implantable medical lead heats by less than about 5° C. (e.g., less than about 4° C., less than about 3° C., or less than about 2° C.) when the lead is subjected to MRI under the following conditions: 1.5 T MRI scan at normal operating mode, and where heating at the electrode is tested by an in-vitro measure that is predictive of in-vivo electrode heating. In some embodiments, an electrode of a such a lead results in decreased heating relative to an electrode of a substantially similar lead that does not include the carbon nanotube structure. In some embodiments, heating at the electrode of such a lead is reduced by 50% or more relative to the electrode of the substantially similar lead without the carbon nanotube structure when the lead is subjected to 1.5 T MRI scanning or an equivalent thereof. In some embodiments, heating is reduced by 60% or more, by 70% or more, or by 80% or more. The carbon nanotube structure may be any suitable carbon nanotube wire as described herein.

DEFINITIONS

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise.

As used in this specification and the appended claims, the term "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like. As used herein, "consisting essentially of," as it relates to a product, method or the like, means that the components of the, product, method or the like are limited to the enumerated components and any other components that do not materially affect the basic and novel characteristic(s) of the composition, product, method or the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

Also herein, the recitations of numerical ranges by endpoints include all numbers subsumed within that range (e.g., 1 to 5 includes 1, 1.5, 2, 2.75, 3, 3.80, 4, 5, etc. or 10 or less includes 10, 9.4, 7.6, 5, 4.3, 2.9, 1.62, 0.3, etc.). Where a range of values is "up to" a particular value, that value is included within the range.

As used herein, the term "about" encompasses the range of experimental error that occurs in any measurement or ranges within manufacturing tolerances.

INCORPORATION BY REFERENCE

Any patent or non-patent literature cited herein is hereby incorporated herein by reference in its entirety to the extent that it does not conflict with the disclosure presented herein.

In the detailed description above several specific embodiments of systems, leads, conductors, strands, wires and methods are disclosed. It is to be understood that other embodiments are contemplated and may be made without departing from the scope or spirit of the present disclosure. The detailed description, therefore, is not to be taken in a limiting sense.

In the following non-limiting examples that provide illustrative embodiments of the leads, conductors, strands and wires described above. These examples are not intended to provide any limitation on the scope of the disclosure presented herein.

EXAMPLES

Figure 11:
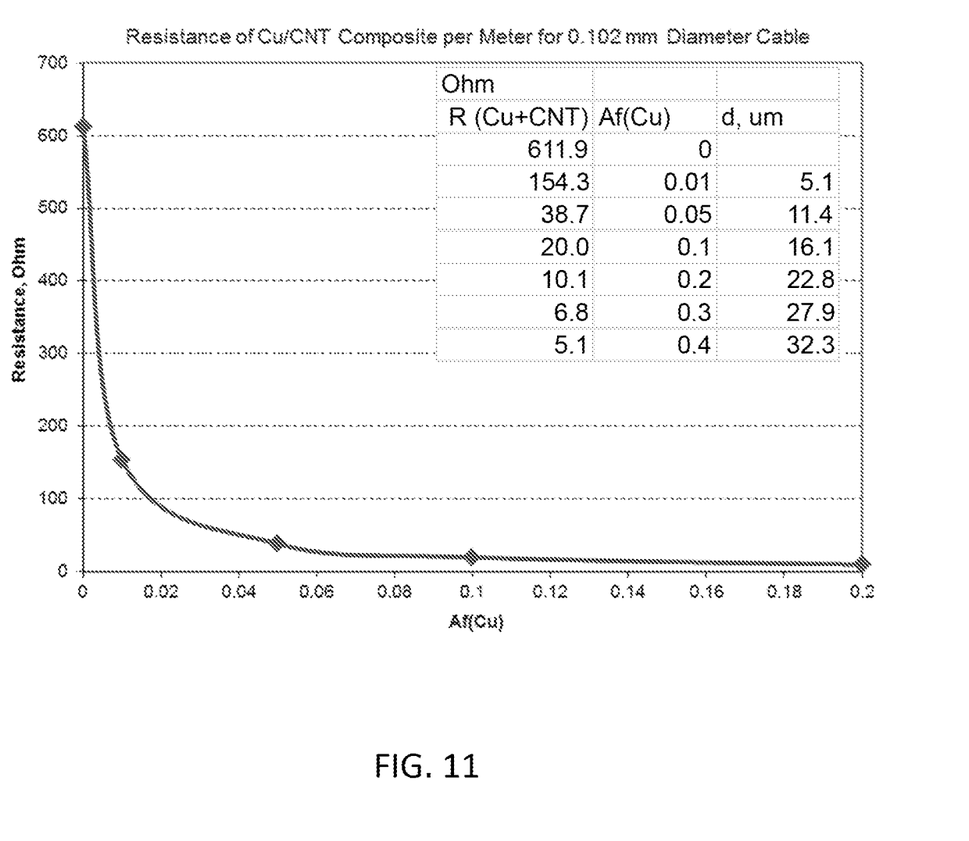
FIG. 11 is a graph of resistance verses copper area fraction of conductors that include carbon nanotube wires and a copper wire.

Example 1: Identifying Suitable Proportion of Metal to Carbon Nanotube to Achieve Desired Electrical Properties Because carbon nanotubes (CNTs) are typically less conductive that metals, an attempt was made to determine the ratio of carbon nanotube to metal that would have a suitable conductivity for purposes of an implantable medical lead. Different area fraction of Cu wires (or any conductor wire) were spun with CNT strands to produce metal core CNT composite yarn. Resistance was determined as a function of percent of cross-sectional area of Au. Results are shown in FIG. 11, which shows the resistance of CNT/Cu composite rope as a function of Cu wire area fraction. This is based on a 0.102 mm (0.004") diameter rope (wire) with one meter length. As the Au wire became 10% of the cross-section area, the resistance reduced from 612 Ohms to about 26 Ohms. The Af(Cu) is the area fraction of the rope cross-section area. The table shows the Af(Cu) of Cu wire and its diameter.

For a 0.004" diameter and one meter long rope of CNT, when we add a 16 um diameter Cu wire, the resistance is reduced from about 612 Ohms to about 5 Ohms.

As shown in FIG. 11, combining CNTs and metal wires together to form a conductor result in suitable resistance/conductivity for use in implantable medical leads and should improve fatigue life due to the mechanical properties of CNTs.

Example 2: Testing Carbon Nanotube/Metal Composite Conductors in Leads

Leads having a conductor containing six carbon nanotube yarns, each with a diameter of 10-30 microns, a single copper alloy wire with a diameter of 10-30 microns and bundled together with an insulator coating with a total diameter of 0.10-0.13 mm were constructed as follows. Medtronic, Inc. model 5076 leads were obtained. The outer lead body insulation was removed by cutting at the proximal and distal bonds. This exposed the outer coil conductor was removed in two different manners. In the first, the conductor was cut approximately one inch proximal to the distal electrode, as well as approximately 1 inch distal to the proximal connector. It was unwound off of the inner insulation. In the second method, the conductor was cut at the distal electrode and the proximal connector joints. It was also unwound off of the inner insulation.

The outer conductor was replaced with either one multi-strand carbon fiber bundle consisting of between 500-3000 individual carbon fibers or a single carbon nanotube/Copper alloy composite conductor as described above. The conductor was joined onto either the remaining proximal outer conductor coil stub or directly to the proximal connector, depending upon the previous removal method. This bond was made by adhering the conductor to the substrate with a conductive silver epoxy. The joint was wrapped in PTFE thread sealant tape to immobilize and reinforce during assembly. The conductor was then wrapped loosely around the inner insulation with a pitch varying from 0.5-3 turns per inch.

At the distal joint, the conductor was bonded to either the remaining distal outer conductor coil stub or directly to the distal electrode in a manner consistent with the proximal end. After cutting the remaining exposed conductor, the system was placed in an air oven for 1 hour at 150° C. to cure the epoxy.

After curing, the PTFE tape was removed and a urethane outer insulator was slid over the lead. Bonds of the outer insulator were made at the proximal and distal ends using medical adhesive.

Performance of the leads was then tested.

In general, the voltage drop from the tip electrode to the ring electrode, from the tip electrode to the calomel, from the ring electrode to the calomel, from the tip to the indifferent electrode, and the indifferent electrode to the calomel was substantially similar between control 5076 leads and the leads modified to include the CNT/metal or carbon fiber (CF) when tested in vitro under unipolar and bipolar modes (data not shown).

Example 3: Magnetic Resonance Heating at Electrodes

Leads constructed as described above in Example 2 were subjected to RF field equivalent to those from a typical 1.5 T MRI scanner coil to determine the extent to which the tip and ring electrode heat. Heating at the electrodes was tested using in-vitro measurements predictive of in-vivo temperature rise. The results are presented in FIG. 12, where the left bar is the control Medtronic, Inc. Model 5076 lead, the middle bar is the lead modified to include CF, and the right bar is the lead modified to include the CNTs. dT99.9% definition: In 99.9% of the cases, the temperature rise is less than this value.

Figure 12:
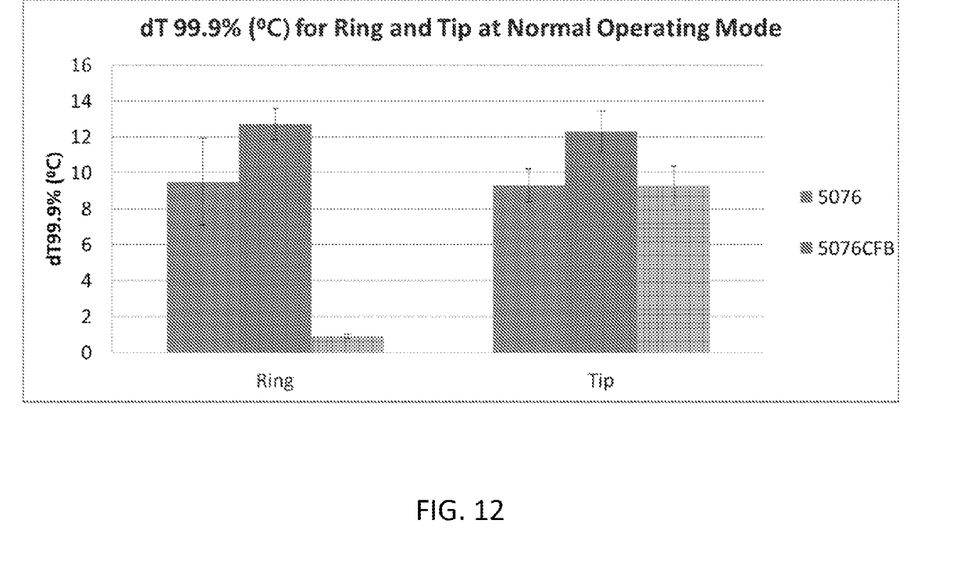
FIG. 12 is a graph of heating at ring and tip electrodes of a control lead (left), a lead having a carbon fiber wrapped conductor (middle), and a lead having a carbon nanotube/metal conductor (right).

As shown in FIG. 12, long strand carbon nanotube conductors significantly reduces ring electrode heating, while wrapped carbon fiber bundle does not. At the tip electrode, reduced heating was not observed because the conductor was not replaced by a carbon nanotube/copper conductor. As a contrast to ring electrode, this further demonstrates the effectiveness of the long strand carbon nanotube in reducing the heating of the electrode to which it is applied.

Thus, systems, devices and methods for IMPLANTABLE MEDICAL LEAD CONDUCTOR HAVING CARBON NANOTUBE WIRE are described. Those skilled in the art will recognize that the preferred embodiments described herein may be altered or amended without departing from the true spirit and scope of the disclosure, as defined in the accompanying claims.

The invention claimed is:

1. An implantable medical lead, comprising:
a proximal end portion having a contact;
a distal end portion having an electrode;
a conductor electrically coupling the electrode to the contact; and
a carbon nanotube structure coupled to the electrode and the conductor, but not the contact, wherein the carbon nanotube structure extends proximally in the lead from the electrode a distance sufficient to prevent heating of the electrode by more than 5° C. when the lead subjected to 1.5 T magnetic resonance imaging scanning at normal operating mode, and wherein heating at the electrode is tested by an in-vitro measure that is predictive of in-vivo electrode heating.

2. The implantable medical lead of claim 1, wherein the carbon nanotube structure extends proximally in the lead from the electrode to a location more distal than the contact.

3. The implantable medical lead of claim 1, wherein at least a portion of the conductor forms the electrode.

4. The implantable medical lead of claim 1, wherein the conductor comprises one or more metal wires, and wherein the carbon nanotube structure comprises one or more carbon nanotube wires extending in a direction substantially the same as the one or more metal wires.

5. The implantable medical lead of claim 4, wherein the one or more metal wires and the one or more carbon nanotube wires are twisted or braided around one another.

6. The implantable medical lead of claim 4, wherein the one or more metal wire is formed from Cu, Au, Pt, Ag, MP35N, Ta, Nb, Ti, Mo, W, Pt—Ir, Pd, or a combination thereof.

7. An implantable medical lead, comprising:
a proximal end portion having a contact;
a distal end portion having an electrode;
a conductor electrically coupling the electrode to the contact; and
a carbon nanotube structure coupled to the electrode and the conductor, but not the contact, wherein the carbon nanotube structure extends proximally in the lead from the electrode a distance sufficient to reduce heating of the electrode by 50% or more relative to a substantially similar electrode that does not contain the carbon nanotube structure when the lead subjected to 1.5 T magnetic resonance imaging scanning or an equivalent thereof.

8. The implantable medical lead of claim 7, wherein the conductor comprises one or more metal wires, and wherein the carbon nanotube structure comprises one or more carbon nanotube wires extending in a direction substantially the same as the one or more metal wires.

9. The implantable medical lead of claim 8, wherein the one or more metal wires and the one or more carbon nanotube wires are twisted or braided around one another.

10. The implantable medical lead of claim 8, wherein the one or more metal wire is formed from Cu, Au, Pt, Ag, MP35N, Ta, Nb, Ti, Mo, W, Pt—Ir, Pd, or a combination thereof.

* * * * *